US006016802A

United States Patent [19]

Jackson

[11] Patent Number: 6,016,802

[45] Date of Patent: Jan. 25, 2000

[54] BREATHING APPARATUS AND FACEPIECE THEREFOR

[75] Inventor: Peter Joseph Jackson, Worthing, United Kingdom

[73] Assignee: International Safety Instruments, Inc., Lawrenceville, Ga.

[21] Appl. No.: 08/932,039

[22] Filed: Sep. 17, 1997

[30] Foreign Application Priority Data

Sep. 18, 1996 [GB] United Kingdom .................. 0619459

[51] Int. Cl.[7] ............................ A62B 7/04; A61M 16/00

[52] U.S. Cl. ............................... 128/205.25; 128/205.24; 128/203.11; 128/201.19; 128/204.26

[58] Field of Search ........................ 128/205.25, 205.24, 128/201.19, 203.29, 205.23, 206.15, 207.12, 207.16, 203.11, 204.26, 204.24, 202.28; 137/223, 614.2

[56] References Cited

U.S. PATENT DOCUMENTS

| | | | |
|---|---|---|---|
| 3,109,425 | 11/1963 | Gongoll et al. | 128/201.19 |
| 4,572,176 | 2/1986 | Walther | 128/204.26 |
| 4,629,159 | 12/1986 | Anderson et al. | 137/223 |
| 4,762,145 | 8/1988 | Stradella | 137/614.2 |
| 4,834,085 | 5/1989 | Webster, II | 128/203.11 |
| 5,042,473 | 8/1991 | Lewis | 128/204.26 |
| 5,499,624 | 3/1996 | Kruger et al. | 128/205.25 |
| 5,572,990 | 11/1996 | Berlin | 128/201.19 |
| 5,584,288 | 12/1996 | Baldwin | 128/203.11 |
| 5,749,359 | 5/1998 | Hansen | 128/205.25 |

*Primary Examiner*—John G. Weiss
*Assistant Examiner*—V. Srivastava
*Attorney, Agent, or Firm*—James B. Middleton; Walter A. Rodgers

[57] ABSTRACT

A breathing apparatus comprises a supply of breathable gas and a facepiece by which breathable gas is supplied to a wearer, the facepiece including a supply valve for delivering gas to the interior of the facepiece, and an exhaust opening closeable by an exhaust valve for allowing the egress of exhaled gas from the facepiece. The exhaust valve comprises a movable valve member which, in a first position, closes the exhaust opening in the facepiece, in a second position is displaced toward the interior of the facepiece relative to the first position while still in sealing engagement with the exhaust opening to open the supply of breathable gas, and in a third position is displaced outwardly of the facepiece relative to the first position to open the exhaust opening to allow the egress of exhaled gas. The valve member is biased towards the second position by a single significant biasing means. A sealing element is preferably interposed between the valve member and the exhaust opening.

38 Claims, 3 Drawing Sheets

BREATHING APPARATUS AND FACEPIECE THEREFOR

This invention relates to breathing apparatus whereby breathable gas is supplied automatically to the wearer in accordance with his respiratory requirements. More particularly, it relates to apparatus of the "Positive Pressure" type, wherein a pressure which is a predetermined level above the pressure of the ambient atmosphere is maintained within the facepiece so as to prevent inward leakage of air, noxious gases or smoke, etc., from the surrounding atmosphere into the interior of the facepiece.

Breathing apparatus of the positive pressure type is well known, and is commonly used by firefighters for entering smoke-filled buildings or while dealing with chemical spills. For these purposes, it is normal to use apparatus of the self-contained type where a supply of air or other breathable gas is carried by the wearer in one or more high pressure cylinders.

A typical apparatus comprises a cylinder containing compressed air at high pressure, typically 200 to 300 bar, which is carried on the wearer's back by means of a backplate or frame, to which is attached an adjustable webbing harness. The cylinder is fitted with a stop valve, to which is connected a first stage pressure regulating valve which reduces the air supply pressure to a substantially constant value of, say, 7 bar. The air is supplied by this first stage regulator, via a flexible hose, to a second stage regulator, commonly known as a demand valve, which is attached to a full facepiece of rubber or a similar resilient material. The facepiece is conventionally, held to the wearer's face in a lead-tight manner by means of an adjustable head harness.

The facepiece, which has a transparent visor, is fitted with a non-return valve through which the wearer's exhaled breath is exhausted to atmosphere. This valve is spring loaded so as to open only when pressure within the facepiece exceeds the predetermined level above that of the surrounding atmosphere, this difference normally being set at about 4 millibar.

The demand valve responds to pressure changes within the facepiece and is spring loaded or biased so as to open and admit air from the first regulator when pressure within the facepiece falls, due to inhalation by the wearer or outward leakage, to a level below, say, 3 millibar above the ambient outside pressure. By this means, pressure within the facepiece is maintained at a level of between 3 and 4 millibar above the ambient outside pressure.

In order to allow a fully attired wearer to breathe atmospheric air in areas where it is safe to do so, and thus conserve his limited air supply, and also to facilitate decontamination of the facepiece after use, the connection between the demand valve and the facepiece is commonly by means of a bayonet or similar coupling which can be rapidly assembled or disassembled by the wearer.

The facepiece is also conventionally fitted with a speech transmission diaphragm, comprising a taut membrane of thin metal or high strength plastics material, supported in a rigid housing in the front of the facepiece and protected by a grille. The clear transmission of speech is of critical importance in many situations in which breathing apparatus is worn, particularly in firefighting.

It is also conventional to provide a gauge to indicate the air pressure in the cylinder, in order to allow the wearer to monitor his air supply. An audible alarm, usually a whistle or bell, indicates when cylinder pressure has fallen to or below a predetermined level.

The typical apparatus described above has a number of limitations and disadvantages, which the present invention seeks to overcome.

The facepiece, incorporating the speech transmission diaphragm, spring loaded exhalation valve and connection for the demand valve, is a complex assembly of many parts and is thus costly to produce. Its cost is often so high as to inhibit the provision of personal facepieces to each of the individuals in a firefighting team, for example. This situation, in which facepieces must be "shared" by two or more team members, may give rise to objections relating to communicable diseases and certainly necessitates very thorough decontamination of the facepiece after every use. The demand valve, which is in the respiratory circuit and thus also susceptible to contamination, is not easy to clean effectively, due to the need to prevent the ingress into the passages in the valve of water which may subsequently freeze, adversely affecting its operation.

The necessity, for firefighters in particular, to be completely attired in their protective clothing and equipment prior to entering an area where respiratory protection becomes necessary, requires that the demand valve to disconnectable from the facepiece to allow the wearer to breathe atmospheric air whilst conserving his compressed air supply. This procedure, in turn, necessitates that an additional device be incorporated into the demand valve to override its positive pressure operation so as to prevent free escape of air and to restore demand operation when the valve is reconnected to the facepiece or when the wearer first inhales from the valve.

Disconnection of the demand valve from the facepiece exposes the outlet of the valve to the ingress of dirt or water which may later affect operation of the valve, or may be inhaled by the wearer. The demand valve, being mounted externally to the facepiece, is exposed to extremes of temperature and forms a significant protrusion which is susceptible to catching on obstructions with the subsequent risk of dislodging the facepiece.

It is the object of the present invention to overcome the disadvantages described by providing a single integrated assembly incorporating the demand valve, exhalation valve and speech transmission diaphragm with a means of allowing the wearer to conserve his supply of breathable gas and breathe from the atmosphere at will without either removing the demand valve assembly from the facepiece, or removing the facepiece from his face. The assembly may thus be permanently, or semi-permanently attached to the facepiece, greatly increasing the integrity of the apparatus and reducing the overall size, weight and cost due to the reduced number of component parts.

It is a further object of the invention to provide a fixed and minimal differential between the opening pressure of the exhalation valve and the opening pressure of the demand valve, and to further reduce the overall work of breathing for the wearer by providing an exhalation valve of considerably greater area than could normally be accommodated in a conventional apparatus. The preferred embodiments of the invention also place the working parts of the breathing valves within the facepiece where they are protected from extremes of temperature, and also provide a means of preventing ingress of water into the demand valve, so that the complete facepiece and valve assembly may be readily washed and decontaminated by immersion.

STATEMENT OF INVENTION

According to a first aspect, a facepiece for a breathing apparatus comprises a supply valve for delivering breathable gas to the interior of the facepiece, and an exhaust valve for allowing the egress of gas from the facepiece, wherein the exhaust valve is a movable diaphragm having a first position wherein it engages with a movable sealing element to seal an exhaust opening in the facepiece, a second position displaced toward the interior of the facepiece relative to the first position and still in sealing engagement with the facepiece, and a third position displaced outwardly of the facepiece relative to the first position and out of sealing engagement with the facepiece, the diaphragm being biased towards the second position by biasing means, and the diaphragm engaging operating means to open the supply valve when in the second position.

In a second aspect, there is provided a breathing apparatus to supply breathable gas to a wearer, comprising a reservoir of breathable gas at superambient pressure and a facepiece sealable to the wearer's face to cover the nose and mouth, the facepiece comprising a supply valve for delivering air to the interior of the facepiece, and an exhaust valve for allowing the egress of gas from the facepiece, wherein the exhaust valve is a movable diaphragm having a first position wherein it engages with a movable sealing element to seal an exhaust opening in the facepiece, a second position displaced toward the interior of the facepiece relative to the first position and still i sealing engagement with the facepiece, and a third position displaced outwardly of the facepiece relative to the first position and out of sealing engagement with the facepiece, the diaphragm being biased towards the second position by biasing means, and the diaphragm engaging operating means to open the supply valve when in the second position.

In a third aspect, a control arrangement for actuating a demand valve in a facepiece of a breathing apparatus comprises a valve element having an open position wherein the valve element lies outside the facepiece, an initial sealing position wherein the valve element is in sealing contact with an exhaust opening in the facepiece, and an operating position wherein the valve element and exhaust opening are still in sealing contact and the valve element is displaced from the second position toward the interior of the facepiece, the valve element engaging an actuator to open the demand valve while the valve element is in the operating position.

A fourth aspect of the invention provides a demand valve for a facepiece of a breathing apparatus comprising closure means to prevent ingress of decontaminating fluid into the demand valve.

Embodiments of the invention will now be described in detail, with reference to the accompanying drawings, in which.

Figure 1:
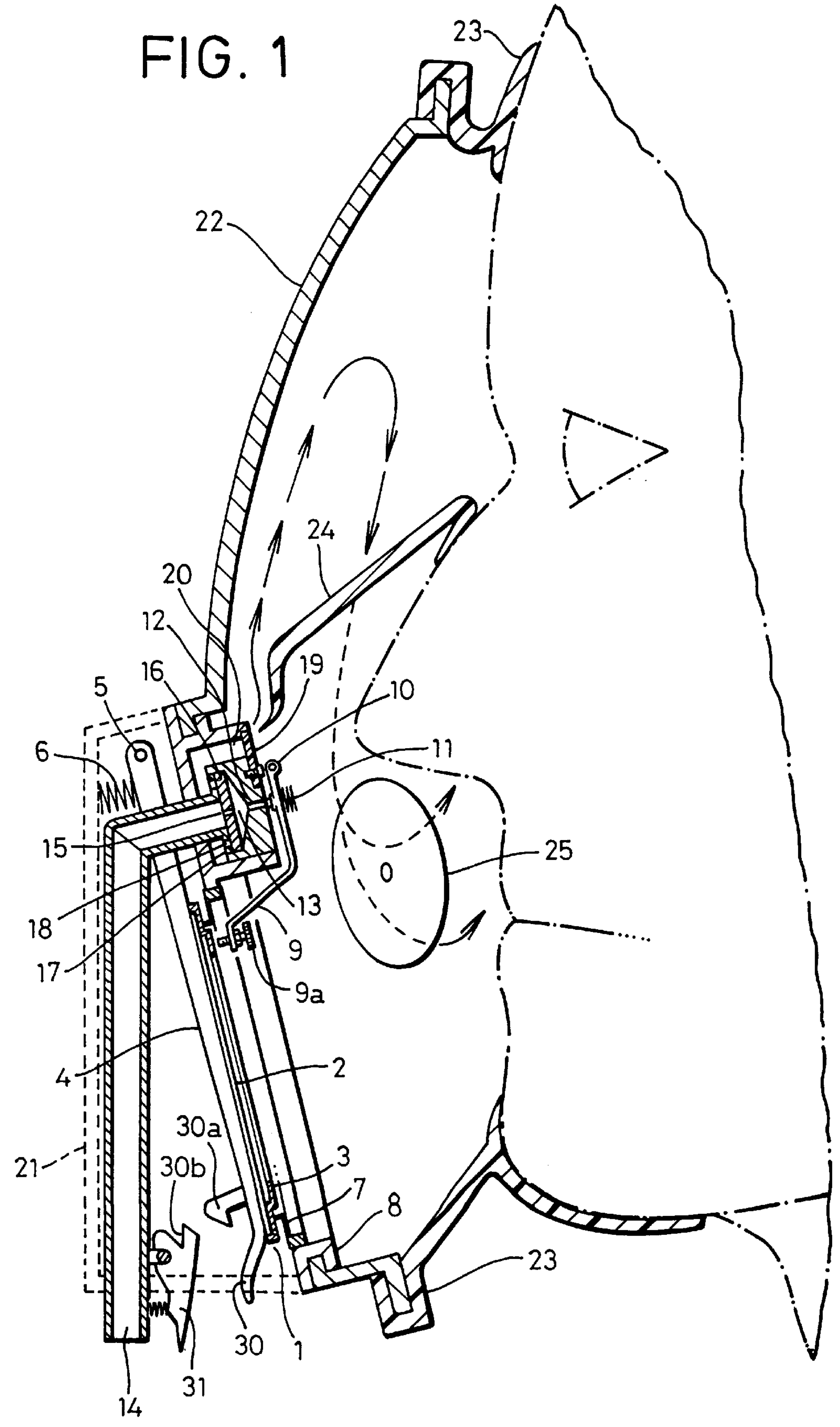
FIG. 1 shows a sectional side elevation of a preferred embodiment of the invention.

Referring now to FIG. 1, a speech transmission diaphragm assembly 1 comprises a taut membrane 2 held in a rigid circular housing 3. This diaphragm assembly 1 is rigidly fixed to a lever 4, pivoted at 5 and biased by a spring 6 such that the diaphragm is urged towards a deformable resilient seal 7, clamped at its periphery to a housing 8. The seal 7 is so configured that it can, after making sealing contact with the diaphragm assembly 1, allow further "inward" movement of the diaphragm (towards the wearer) beyond the initial "closed" position seen in FIG. 1. The force of the spring 6 is such as to urge the diaphragm to close the opening defined by the seal 7, and is sufficient to deform or deflect the seal 7 further, beyond this initial "closed" position in the absence of a pressure difference across the diaphragm.

A lever 9 is pivoted at 10 and is biased by a light spring 11 so as to close of a small pilot jet 12. When the pilot jet 12 is closed by the lever 9, the pressure within a pilot chamber 13, resulting from air entering the chamber 13 from an air inlet 14 through a metering orifice 15 in the centre of a resilient disc 16, clamps the disc 16 against a face of a flange 17. The relative sizes of the pilot jet 12 and metering orifice 15 are such that the pilot jet 12 can exhaust the pilot chamber 13 faster than the metering orifice 15 can replenish it. Any escape of air through the pilot jet 12 causes a reduction in pressure within the chamber 13, allowing the resilient disc 16 to bow away from the flange 17 under the influence of air pressure at the inlet 14, exposing a series of openings 18 in the flange through which air may pass from the inlet 14 to an outlet 20 and thence into the interior of the facepiece. The free end of lever 9 is provided with an adjusting screw 9*a* to vary the position of the diaphragm assembly at which initial contact is made with the lever 9. Clearly, embodiments are foreseeable wherein an adjustable abutment is provided on the diaphragm, and a fixed abutment on lever 9. When the screw 9*a* is correctly adjusted, the diaphragm is just out of contact with the lever when the pressure within the facepiece exceeds atmospheric pressure by the required pressure difference. "Inward" movement of the diaphragm 1, beyond that initial contact position will cause the diaphragm to come into contact with the screw 9*a* at the end of lever 9, and pivot the lever away from the pilot jet 12, allowing air to exit through the jet 12 from the pilot chamber 13.

A resilient non-return flap 19, which protects the valve outlet 20 from the ingress of water, deflects to allow air to pass freely from the valve into the facepiece.

It will be understood from the foregoing that the supply of air to the facepiece is controlled by a two-stage main valve composed of the resilient disc 16, whose opening and closing is in turn controlled by the opening and closing of a pilot arrangement, composed of the pilot chamber 13 and jet 12. The pilot arrangement is in turn controlled by the movement of the lever 9, which is moved by the diaphragm 1 when diaphragm 1 moves inwards in response to a reduction in pressure within the facepiece.

It is emphasised that in operation, forces act on the diaphragm due to the resilient nature of the seal 7, the biasing spring 6 of the diaphragm assembly 1, and the force exerted by pressure differences on the diaphragm. The biasing spring 6 is sufficiently strong to move the diaphragm, in the absence of any pressure difference across the diaphragm, from a first position in which initial contact is made with seal 7 but with seal 7 unmoved, into a third position in which seal is moved toward the wearer and the diaphragm 1 contacts the screw 9*a* of lever 9. The diaphragm 1 and seal 7 remain in sealing contact throughout this movement.

When the facepiece is sealed to the wearer's face, initially no pressure difference exists between the interior of the diaphragm and the outside atmosphere. The diaphragm 1 is urged inward by the biasing spring 6. Seal 7 is deformed as diaphragm 1 moves inward under the action of spring 6. Diaphragm 1 contacts and moves lever 9 to open the pilot valve 12, and air is admitted into the facepiece until the pressure within the facepiece rises to a superatmospheric level sufficient to urge the diaphragm 1 to move outwards against the force of spring 6. As the diaphragm 1 moves outwardly under the increasing pressure within the facepiece, lever 9 is urged by spring 11 to follow the movement of the diaphragm until lever 9 closes the pilot jet 12. A state of equilibrium will then exist if pressure within the facepiece is maintained at this level.

When the wearer inhales, pressure within the facepiece falls below the equilibrium level. The diaphragm 1 then moves inwards under the action of spring 6, deflecting the resilient seal 7 and opening the pilot valve 12 again to admit air to the facepiece. When inhalation ceases, pressure within the facepiece will rise again, urging the diaphragm 1 outwards, restoring the equilibrium pressure level and allowing the pilot valve 12 to close. The diaphragm remains tightly closed on the seal 7 throughout the inhalation phase.

When the wearer exhales, pressure within the facepiece will rise above the equilibrium level, and this pressure difference across diaphragm 1 urges the diaphragm outwards. After a small outward movement of both the diaphragm 1 and the seal 7, the seal 7 reaches the limit of its movement. Diaphragm 1 thereafter continues to move away from the resilient seal 7 to expose a gap around the periphery of the diaphragm 1, through which the excess air is vented to atmosphere. A cover 21, which is shown in dotted lines, protects the assembly from damage and from radiant heat, and has suitably positioned openings (not shown) to allow for the unhindered passage of the exhaled air to atmosphere. These openings also provide a path for sounds transmitted through the diaphragm 1, allowing the clear transmission of speech.

In a preferred development of the invention, in order to allow the wearer to breath atmospheric air without removal of the facepiece, a lifting and latching means is provided to move the diaphragm 1 away from the resilient seal 7, and to hold it in this open position. In FIG. 1, such a lifting arrangement is seen at 30, where the diaphragm 1 is provided with a finger tab 30 projecting downwardly from its lower end. By placing a finger to the right (as seen in the Figure) of the tab 30 and moving it to the left, the wearer may move the diaphragm away from seal 7 to allow free ingress and egress of air into the facepiece. It is emphasised that the lever 9 is unmoved by lifting the diaphragm in this way, and thus the demand valve remains closed, conserving the air supply.

In the most preferred embodiment, latching means 30*a* and 30*b* are provided to retain the diaphragm in its lifted position. In the embodiment of FIG. 1, detent 30*a* engages with pivoting latch 30*b* when the diaphragm is lifted by the wearer. Leftwards (as seen in the Figure) pressure at the lower part 30*c* of pivoting latch 30*b* causes the latch 30*b* rotate clockwise and to disengage from the detent 30*b*, and spring 7 then returns the diaphragm 1 to its initial position in contact with seal 6, to continue the normal operating sequence.

In the illustrated embodiment, lifting the diaphragm 1 opens a port of substantial area, directly in front of the wearer's nose and mouth. The latch may be arranged in other configurations than that shown, provided the latch can operate to hold the diaphragm 1 in the open position. While the latch may be engaged and released, or "tripped", by a single action, such as by pressing a projecting button, release arrangements requiring more determined manipulation are foreseen. In order to prevent inadvertent or accidental opening of the diaphragm, the latching means is preferably designed to that a double action is required by the wearer to engage the latch, such as by simultaneously depressing two buttons on opposite sides of the valve assembly. When the diaphragm 1 is in the open position, it is necessarily out of contact with lever 9, and thus the pilot valve 12 remains closed, conserving the air supply. The wearer may then remove the facepiece without loss of pressurised air through the demand valve.

A manually operated bypass, or override, valve (not shown) may be provided, whereby a controlled flow of air may be admitted to the facepiece at will. Additionally or alternatively, a stop vale may be provided between the pressurised air supply tank and the facepiece, since it will be appreciated that if the wearer removes the facepiece without latching the diaphragm 1 open, the diaphragm 1 will be moved by the spring 6 to open the pilot valve 12 and allow a free flow of air.

Figure 2:
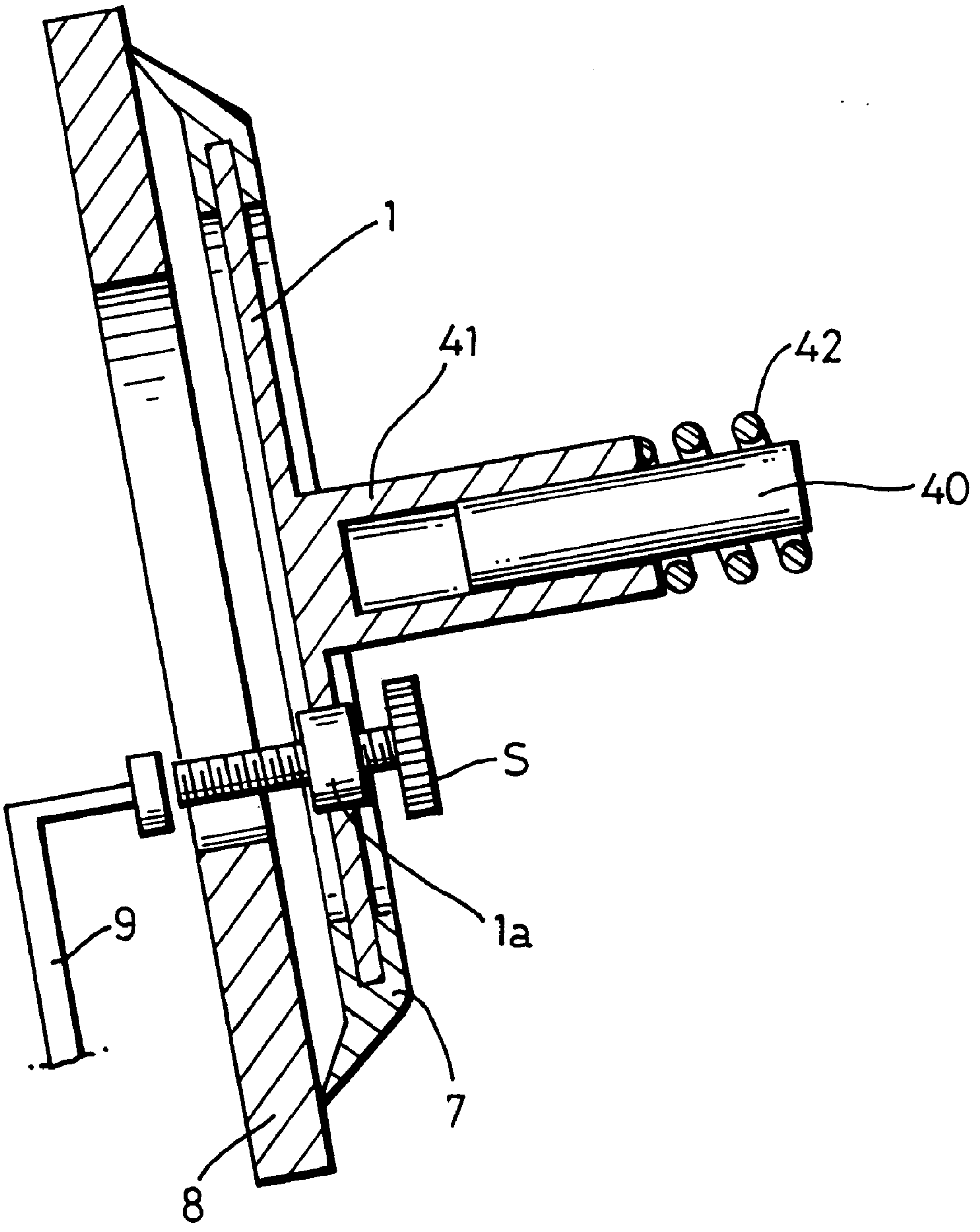
FIG. 2 is an enlarged fragmentary view, showing an alternative method of supporting the diaphragm and seal.

In the embodiment shown in FIG. 2, the diaphragm 1 is mounted on a resiliently biassed telescopic support comprising a bearing post 40 attached to the housing of the facepiece and a sleeve 41 attached to the outer face of the diaphragm assembly. A spring 42 surrounds the post 40 and urges the sleeve 41 and diaphragm 1 and the seal 7 towards the wearer. Other mounting arrangements are foreseen for the diaphragm, in addition to the pivotal movement shown in FIG. 1 and the rectilinear movement illustrated in FIG. 2.

In the embodiment sen in FIG. 2, the seal 7 is permanently attached to the periphery of the diaphragm 1, and has a sealing lip which contacts the body 8 of the facepiece. The flexible nature of the seal 7 allows the diaphragm to move towards the wearer after making initial sealing contact with the facepiece, so that lever 9 may be operated to open the supply valve 16 in a manner similar to that described with reference to the embodiment shown in FIG. 1.

An alternative arrangement for adjusting the position at which the diaphragm opens the demand valve is shown. In this embodiment, the diaphragm 1 is formed with a threaded embossment 1*a*, and an adjusting screw S extends through the embossment 1*a* to contact the end of a lever 9 which operates the demand valve (not shown) in a manner similar to that described in relation to FIG. 1.

Figure 3A:
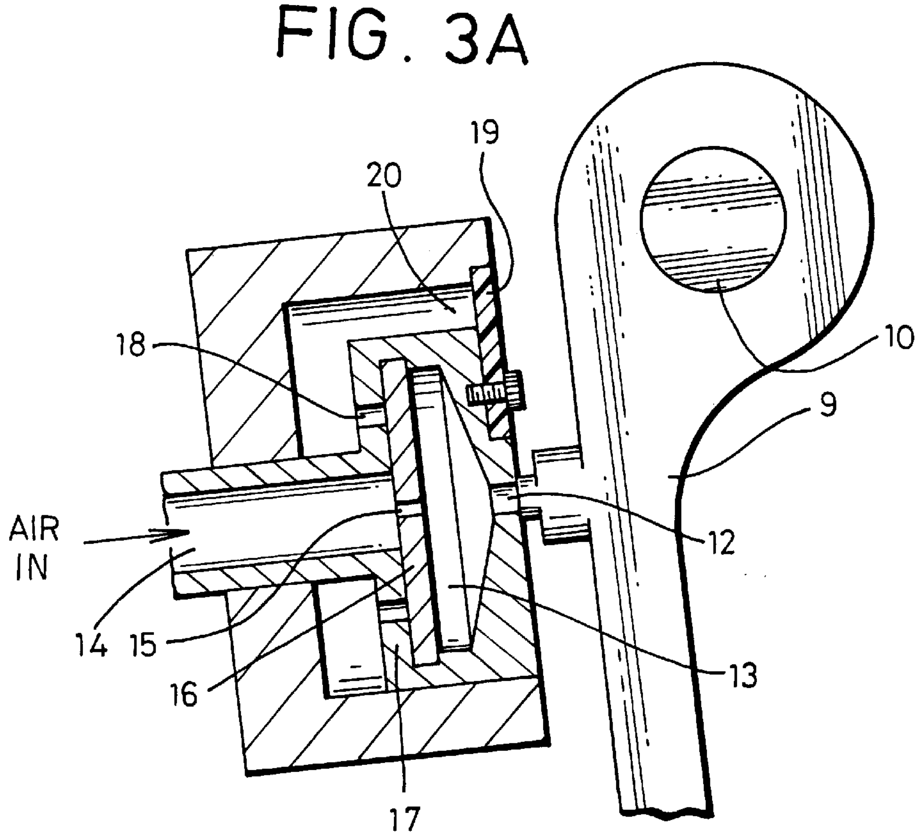
FIG. 3A is an enlarged sectional view of the demand valve in its closed position.
Figure 3B:
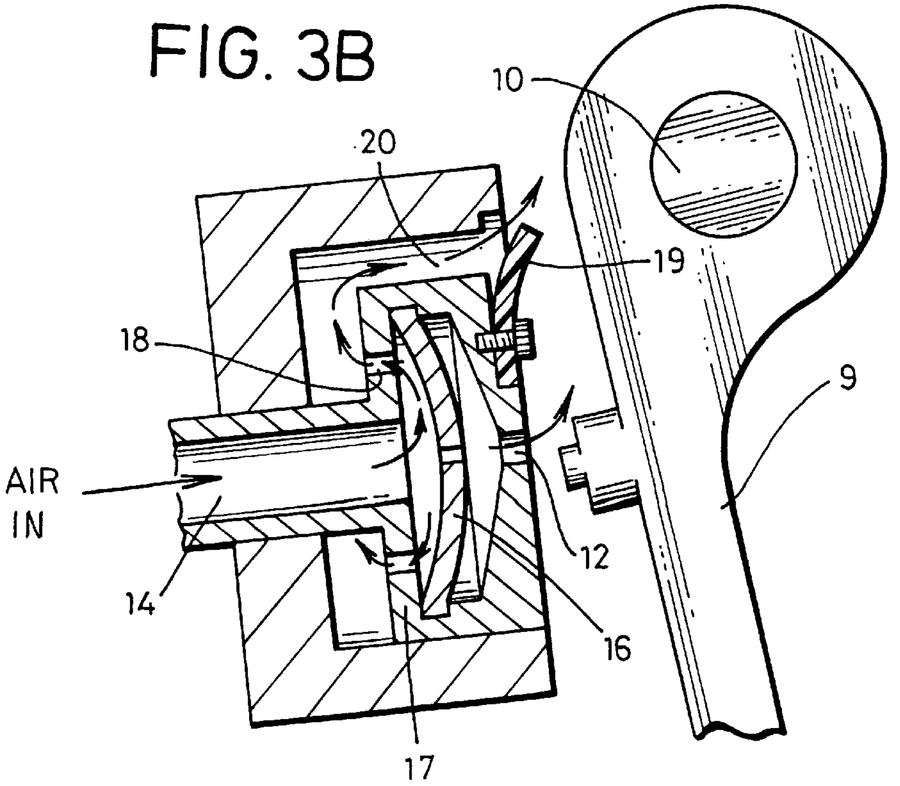
FIG. 3B is a view similar to FIG. 3A, showing the demand valve open to admit air to the facepiece.

FIGS. 3A and 3B shown in greater detail the demand valve 3. In FIG. 3A, lever 9 is urged by spring 11 (FIG. 1) to close the pilot jet 12. Pilot chamber 13 is pressurised by air entering from the metering orifice 15, and resilient sealing disc 16 is urged by this pressure to close the exit ports 18 in the flange 17. Outlet 20 is closed by a resilient flap 19.

When lever 9 is moved by diaphragm 1, pilot jet 12 is opened and air in the pilot chamber 13 escapes through jet 12 faster than it enters via metering orifice 15, thus depressurising the pilot chamber 13. High pressure in the supply tube 14 then deforms the disc 16, and air can pass from supply tube 14 to outlet ports 18 and thence to outlet 20, where the pressure raises resilient flap 19 and allows air to exit to the interior of the facepiece.

Alternative construction for the demand valve are foreseen, provided that the diaphragm can be arranged so as to open the demand valve when the diaphragm 1 and seal 7 have moved inwardly from their position of initial sealing contact, and can close the demand valve as the diaphragm 1 and seal 7 move outwardly together before the diaphragm loses contact with the seal 7.

The facepiece may be a simple assembly of a clear plastics visor 22, attached around its periphery to a resilient seal 23 and secure to the wearer's face by means of an adjustable head harness (also not shown). An opening in the visor 22 accommodates the integrated valve assembly previously described, which may be secured in the opening by means of screws or clips. In the preferred embodiment of the invention shown, the facepiece is provided with an inner half-mask 24.

Air entering the facepiece from the valve outlet 20 is directed into the upper area of the visor and passes through non-return flaps 25 into the half-mask 24, to be inhaled by the wearer. Exhaled air passes directly to atmosphere around the diaphragm 1, which is situated in front of the wearer's mouth for optimum speech transmission. This circuitous passage of the air through the facepiece prevents misting of the visor, ventilates the upper area of the wearer's face and minimises the amount of carbon dioxide inhaled by the wearer.

In the embodiments described, the facepiece covers the entire face of the wearer. The combined speech transmission diaphragm, exhalation valve and demand valve control arrangement described above may however also be embodied in a facepiece which covers only the wearer's nose and mouth. In such cases it is foreseen that separate eye protection may be provided. This arrangement may be advantageous for example in breathing apparatus intended for aircrew.

It is further envisaged that the combined exhaust valve and demand valve may form part of a hood or helmet which extends to cover the entire head of a wearer. A hood formed from flexible material is foreseen, sealed round the wearer's neck, and inflated by the gas supply from a demand valve actuated by a diaphragm arrangement as previously described. Where the demand valve is incorporated in a helmet, the helmet may be fully pressurised, or may have a sealing membrane engaging the wearers' head to enclose the nose and mouth and optionally the eyes. The volume within the sealing membrane will be supplied with pressurised air by the demand valve.

In yet a further alternative, the demand valve may be incorporated into a hood or helmet forming part of a protective garment for the upper body, or of a complete body suit. The demand valve may supply pressurised air at a predetermined temperature to the wearer for respiration, and the same or a further demand valve assembly may supply air to the interior of the garment or suit to cool the wearer.

In any of the above-described embodiments, the supply of breathable gas may be from self-contained cylinders carried by the wearer, or may be from a supply reservoir remote from the wearer and connected to the demand valve via a hose.

It is envisaged that the components of the demand valve may be moulded from plastics materials, to reduce weight and cost.

I claim:

1. In a facepiece for a breathing apparatus by which breathable gas is supplied to a wearer and exhaled gas is exhausted therefrom, said facepiece including a supply valve for delivering breathable gas to the interior of said facepiece and an exhaust opening closeable by an exhaust valve for allowing the egress of exhaled gas from said facepiece, the improvement wherein said exhaust valve comprises an inwardly biased valve member movable relative to said exhaust opening and having a first position in which said valve member closes said exhaust opening and is in sealing engagement therewith, a second position in which said valve member is displaced towards the interior of said facepiece relative to said first position with said valve member still in sealing engagement with said exhaust opening, a third position in which said valve member is displaced outwardly of said facepiece relative to said first position and wherein said exhaust opening is open for allowing egress of exhaled gas, a single biasing means for biasing said vale member towards said second position, and operating means engageable by said valve member when said valve member is in said second position for opening said supply valve.

2. In a facepiece according to claim 1 the improvement including a sealing element cooperating with said valve member and the periphery of said exhaust opening to seal said valve member to the exhaust opening while said valve member is in said first position and while it moves between said first and second positions.

3. In a facepiece according to claim 2, the improvement wherein the sealing element is mounted on the facepiece to surround the exhaust opening.

4. In a facepiece according to claim 2, the improvement wherein the sealing element is mounted on said valve member.

5. In a facepiece according to claim 1, the improvement wherein said valve member is pivotally mounted to the facepiece.

6. In a facepiece according to claim 1, the improvement wherein said valve member is mounted for rectilinear movement relative to said exhaust opening.

7. In a facepiece according to claim 1, the improvement comprising adjustment means to adjust the distance between the first and second positions of said valve member.

8. In a facepiece according to claim 1, the improvement wherein the operating means which opens the supply valve is an operating lever.

9. In a facepiece according to claim 8, the improvement wherein adjustment means is provided between the operating lever and said valve member to adjust the point on the travel of said valve member at which contact with the operating lever is made.

10. In a facepiece according to claim 9, the improvement wherein the adjustment means comprises a fixed abutment on said valve member and a movable abutment mounted on the lever.

11. In a facepiece according to claim 9, the improvement wherein the adjustment means comprises a fixed abutment on the lever and a movable abutment mounted on said valve member.

12. In a facepiece according to claim 1, the further improvement including means operable to move said valve member to its third position.

13. In a facepiece according to claim 1, the improvement including releasable means operable to retain said valve member in its third position.

14. In a facepiece according to claim 13, the improvement wherein the releasable means comprises a movable latch element engageable with a detent.

15. In a facepiece according to claim 14, the improvement wherein the latch element is mounted on the facepiece and the detent is mounted on said valve member.

16. In a facepiece according to claim 1, the improvement wherein said valve member includes a speech transmission diaphragm.

17. In a facepiece according to claim 1, the improvement wherein the interior of the facepiece is divided into upper and lower compartments, the upper compartment covering the wearer's eyes and having a transparent sight window, and the lower compartment covering the wearer's mouth and nasal openings and having said valve member mounted thereon, the supply valve being situated to deliver breathable gas to the upper compartment, and non-return valves being provided to allow gas to flow from the upper to the lower compartment only.

18. In a facepiece according to claim 1, the improvement wherein the facepiece covers the wearers nose and mouth only.

19. In a facepiece for a breathing apparatus, according to claim 1, wherein a supply valve delivers breathable gas to the interior of said facepiece via an outlet opening of the supply valve, the improvement wherein the supply valve further includes a movable cover to close the outlet opening to prevent the ingress of contaminants, the cover being moved away from the outlet opening by fluid pressure when the supply valve member delivers breathable gas.

20. A facepiece according to claim 19 wherein the movable cover is a resilient flap extending across the outlet opening.

21. A breathing apparatus to supply breathable gas to a wearer, comprising a source of breathable gas at superambient pressure and a facepiece sealable to the wearer to cover the nose and mouth, the facepiece comprising a supply valve for delivering breathable gas to the interior of the facepiece, and an exhaust opening closeable by an exhaust valve for allowing the egress of exhaled gas from the facepiece, wherein the exhaust valve comprises a movable valve member which, in a first position, closes the exhaust opening in the facepiece, said valve member being movable to a second position displaced toward the interior of the facepiece relative to the first position and still in sealing engagement with the exhaust opening, and a third position displaced outwardly of the facepiece relative to the first position and in which the exhaust opening is open to allow egress of exhaled gas, said valve member being biased towards the second position by a single biasing means, and aid valve member engaging operating means to open the supply valve when in the second position.

22. A breathing apparatus according to claim 21, wherein a sealing element cooperates with said valve member and the periphery of the exhaust opening to seal said valve member to the exhaust opening while said valve member is in its first position and while it moves between the first and second positions.

23. A breathing apparatus according to claim 22, wherein the sealing element is mounted on the facepiece to surround the exhaust opening.

24. A breathing apparatus according to claim 23, wherein the sealing element is mounted on said valve member.

25. A breathing apparatus according to claim 21, wherein said valve member is pivotally mounted to the facepiece.

26. A breathing apparatus according to claim 21, wherein said valve member is mounted for rectilinear movement relative to said exhaust opening.

27. A breathing apparatus according to claim 21, wherein adjustment means are provided to adjust the distance between the first and second positions of said valve member.

28. A breathing apparatus according to claim 21, wherein the operating means which opens the supply valve is an operating lever.

29. A breathing apparatus according to claim 28, wherein adjustment means is provided between the operating lever and said valve member to adjust the point on the travel of said valve member at which contact with the operating lever is made.

30. A breathing apparatus according to claim 29, wherein the adjustment means comprises a fixed abutment on said valve member ad a movable abutment mounted on the lever.

31. A breathing apparatus according to claim 30, wherein the adjustment means comprises a fixed abutment on the lever and a movable abutment mounted on said valve member.

32. A breathing apparatus according to claim 21, wherein the facepiece further includes means operable to move said valve member to its third position.

33. A breathing apparatus according to claim 21, wherein the facepiece further includes releasable means operable to retain said valve member in its third position.

34. A breathing apparatus according to claim 33, wherein the releasable means comprises a movable latch element engageable with a detent.

35. A breathing apparatus according to claim 34, wherein the latch element is mounted on the facepiece and the detent is mounted on said valve member.

36. A breathing apparatus according to claim 35, wherein said valve member includes a speech transmission diaphragm.

37. A breathing apparatus according to claim 36, wherein the interior of the facepiece is divided into upper and lower compartments, the upper compartment covering the wearer's eyes and having a transparent sight window, and the lower compartment covering the wearer's mouth and nasal openings and having said valve member mounted thereon, the supply valve being situated to deliver breathable gas to the upper compartment, and non-return valves being provided to allow breathable gas to flow from the upper to the lower compartment only.

38. A breathing apparatus according to claim 37, wherein the facepiece covers the wearer's nose and mouth only.

* * * * *